United States Patent [19]

Skeen

[11] Patent Number: 4,603,690
[45] Date of Patent: Aug. 5, 1986

[54] SLIDING PIVOT KNEE JOINT

[76] Inventor: Solomon L. Skeen, P.O. Box 644, Opp, Ala. 36467

[21] Appl. No.: 629,559

[22] Filed: Jul. 10, 1984

[51] Int. Cl.$^4$ .............................................. A61F 5/00
[52] U.S. Cl. ................................... 128/80 C; 623/39
[58] Field of Search ................. 128/80 C, 80 F, 88; 3/22, 26, 27, 1.911; 403/62; 623/39

[56] References Cited

U.S. PATENT DOCUMENTS 3,552,786  1/1971  Schmid ................................. 403/62

FOREIGN PATENT DOCUMENTS

| 2152408 | 4/1973 | Fed. Rep. of Germany | 623/39 |
| 861086 | 10/1940 | France | 623/39 |
| 691264 | 5/1953 | United Kingdom | 623/44 |
| 2088724 | 6/1982 | United Kingdom | 623/20 |

Primary Examiner—Clifford D. Crowder
Attorney, Agent, or Firm—V. L. Leon; Harry I. Leon

[57] ABSTRACT

A joint structure for a knee brace in which the axis around which motion takes place is not fixed but rather simulates that of the natural joint, lengthening and shortening with it. The joint structure includes two slidably-coupled joint elements, the lower one of which has a ramp member and a pair of furcations. The head of the upper joint element is received between these furcations and connected thereto by a pin which passes through an elongated slot formed in the head. As the joint elements rotate toward each other from their fully extended position, the pin slides from the upper to the lower end portion of the slot, increasing the overall length of the joint structure with flection as does the human knee joint.

The radius of curvature of the forward portion of the lower edge surface of the upper joint element, simulating a short cross-section of the lower surface of the condyle of the human knee joint when viewed in profile, is shared by a concave edge surface on a portion of the ramp member which is recessed between the pair of furcations and by the curved edge surfaces of the central portion of the slot. As the pin returns to engage the upper end portion of the slot, the lower edge surface of the upper joint element is brought into contact with substantially the entire length of the concave edge surface, thereby locking the joint structure against hyperextension, preventing its accidental folding when a wearer shifts his weight onto a weakened knee joint while standing, and providing him with positive control of the movement of the joint during walking.

2 Claims, 6 Drawing Figures

U.S. Patent  Aug. 5, 1986  4,603,690
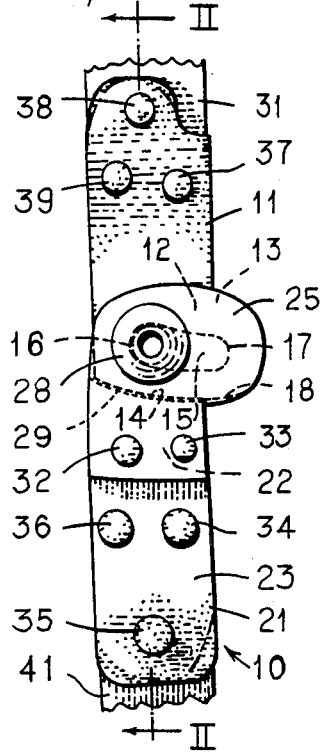
Fig. 1.
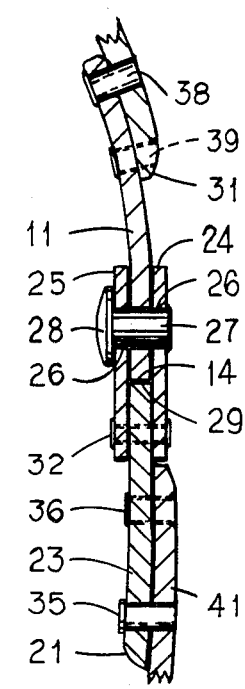
Fig. 2.
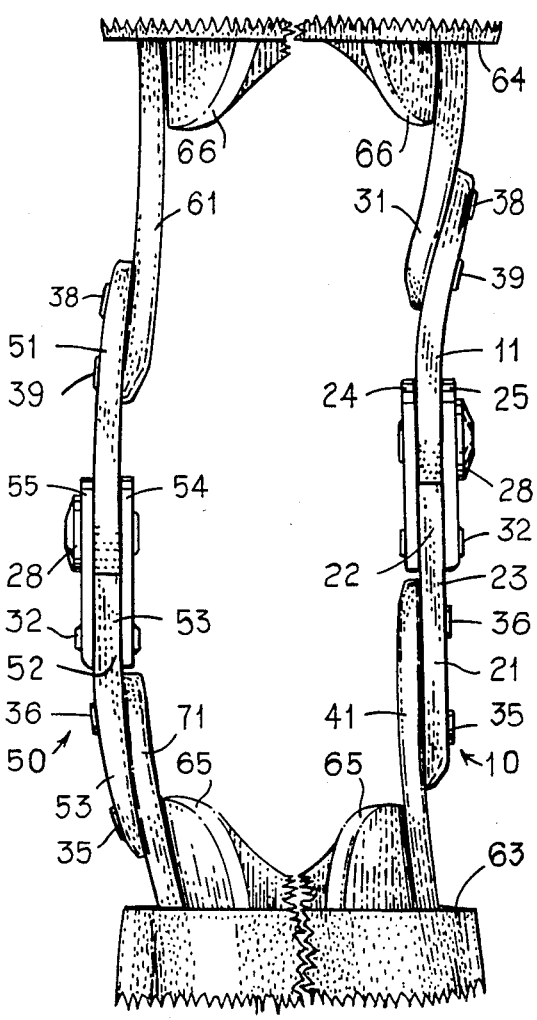
Fig. 3.
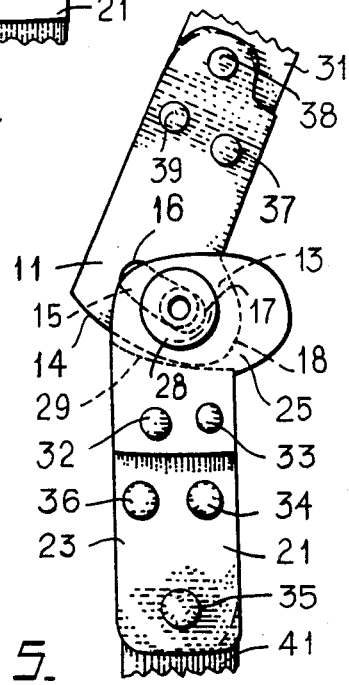
Fig. 4.
Fig. 5.
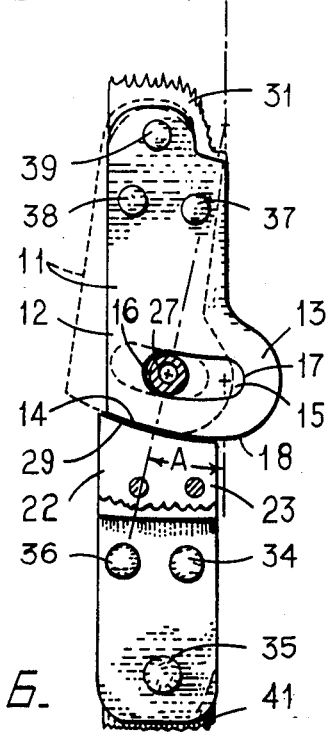
Fig. 6.

SLIDING PIVOT KNEE JOINT

BACKGROUND OF THE INVENTION

1. Field of the Invention

The present invention relates generally to a mechanical joint structure for a brace for the knee, a natural slide and hinge joint in the human body. More particularly, it relates to a joint structure which is slidably-coupled and which has means for constraining the articular motion of the pivotally interconnected joint elements to follow a definite path when they are bent within the degree of flection normally encountered during walking. The invention has specific application as a load-supportive and motion-controlling joint in the rehabilitation of a damaged or diseased knee joint and in prostheses.

2. Description of the Prior Art

Slidably-coupled joint structures having a single pivot for use in knee braces and the like have been described in the prior art. Such structures may include stops for limiting the relative angular movements of the pivotally interconnected joint elements to protect the wearer against hyperextension of the knee joint and against its flection beyond the norm. However, in order to minimize the possibility of premature locking of the joint between its extreme extended and retracted positions, the articular motion is composed of an indefinite combination or rotation and translation. This absence of positive control, while it may be desirable in a brace intended to protect the healthy knee joint of an athlete participating in contact sports, can lead to the collapse of a weakened or diseased knee joint. Such a collapse may be precipitated by the accidental shifting of a person's weight, while standing, onto a leg braced by one of these structures.

Moreover, the tendency of the knee braces of the prior art, including slidably-coupled joint structures with a single pivot, to migrate up and down a wearer's limb makes them less than satisfactory for use in orthopedic devices such as mobile casts. Such a cast must allow a patient to move his knee joint naturally so that he can exercise an affected limb in order to reduce joint stiffness and muscle atrophy; and, at the same time, the cast must prevent the compression and separation of a fracture altogether to insure its proper mending and in particular that the bone does not offset. The slidably-coupled joint structures of the prior art cannot perform both of these functions. Indeed, some of these devices, including those disclosed in U.S. Pat. Nos. 3,552,786 and 4,320,747, shorten when the pivotally interconnected joint elements therein are bent rather than lengthening with the leg as it is being flexed.

The acute need for a joint structure which lengthens a small amount as the leg first starts to bend and shortens when the leg is straightened as does the natural leg exists not only for walking casts but also among prosthetic devices. At present, a person fitted with an artificial limb which does not shorten as it is straightened must cope with a limb which is longer than his natural one. That is, he has to raise himself over the prosthesis, passing it beneath his torso, and then more or less fall forward. Repeating the process, he must position the prosthesis in front of himself once again by moving it so as to cause the joint to bend and then slinging it with enough force to straighten the joint before the heel strikes the floor. If there is too much friction between the joint elements, the requisite bending motion cannot be achieved; and the user has to swing the prosthesis around to his side, adding to his fatigue and creating an even more awkward gait.

A knee joint for an artificial leg which does shorten as the leg is straightened is disclosed in Great Britain Pat. No. 691,264. Unfortunately, this prior art device also lengthens throughout any motion increasing the amount of bending of the joint. Moreover, a person wearing it cannot squat; and in order to sit in a chair, he must begin by sitting sideways with the prosthesis extending straight out or in a slightly bent configuration, then turn so as to position the device in front of himself, and finally lift its thigh portion with his hands so that its shin portion can move under its own weight, bending the knee joint. Even when he has managed to seat himself properly, the wearer of this knee joint still has to contend with the undesirable feature of its being noticeably higher than his natural knee.

SUMMARY OF THE INVENTION

The joint structure according to the present invention comprises two slidably-coupled joint elements, the lower one of which has a pair of furcations between which the head of the upper joint element is received for articular motion relative to the lower joint element. The joint elements are connected by a pin which passes through an elongated slot formed in the head of the upper joint element. This slot is arranged and dimensioned to permit the pin to slide from the upper to the lower end portion of the slot as the joint elements rotate toward each other from their fully extended position, thereby increasing the overall length of the joint structure with flection as occurs naturally during the bending of the knee joint.

Prior to the abutment of the pin with the lower end portion of the slot, the motion of the joint elements is determined by the engagement of the forward portion of the lower edge surface of the head with a concave edge surface on a ramp member, the portion thereof having the concave edge surface being sandwiched between the pair of furcations. Both the concave edge surface and the forward portion of the lower edge surface of the upper joint element have approximately the same radius of curvature as do the curved edge surfaces of the central portion of the slot, so that as the pin returns to engage the upper end portion of the slot, the lower edge surface of the upper joint element is brought into contact with substantially the entire length of the concave edge surface, thereby locking the joint structure with respect to any further increase in the angle between the longitudinal axes of the joint elements and preventing hyperextension of the knee joint. The locking occurs automatically, just by the action of a wearer of a brace incorporating the joint structure setting his foot on the floor.

Moreover, because of the extensive contact between the edge surfaces of the upper and lower joint elements, a brace with the present joint structure cannot bend prematurely causing a collapse when a wearer accidentally shifts his weight while in a standing position. Rather he must first lift his upper leg in order to free the joint structure. Thus the present invention not only enables a knee brace wearer to lock the joint against hyperextension and then to unlock it without having to manipulate any external mechanism but also prevents an unintentional folding of the knee joint in the direction it normally flexes.

The required amount by which the upper leg must be lifted to free the joint structure is less than that encountered during walking, the normal angular movement of the knee joint for such motion being under 25 degrees away from the fully extended position of the joint. The lengths of the forward portion of the lower edge surface of the upper joint element and of the concave edge surface of the ramp member and the orientation of each with respect to the longitudinal axis of the respective joint element on which it is situated are such that sliding contact is maintained between substantial sections of these edge surfaces whenever the joint is under compressive loading during normal walking, thereby providing ample support for a weakened knee.

The head of the upper joint element further includes a rearwardly projecting lobe, the outer edge surface of which has a substantially smaller radius of curvature than does the concave edge surface of the ramp member. When the pin engages the lower end portion of the slot, the pin is positioned at approximately the center of this smaller radius of curvature. Once the angle between their longitudinal axes has been decreased sufficiently, the joint elements rotate, encountering little resistance, about the pin located at this center, thereby facilitating a wearer's actions in sitting down and in rising from a seated position.

It is accordingly a major object of this invention to provide a joint structure for a brace which will prevent both the accidental bending of the knee due to the loss of strength in the leg and the slipping of the foot during walking, running, or stair climbing.

It is a further object to provide a joint structure for a prosthesis which lengthens as a wearer's knee first starts to bend and which shortens as the leg is being fully extended, so that natural leg motion can be imitated as closely as possible.

It is a still further object of this invention to provide a joint structure for a knee brace which has universal application. The unique radius of curvature of the forward portion of the lower edge surface of the upper joint element, simulating a short cross-section of the lower surface of the condyle of the human knee joint when viewed from the side, allows the joint structure according to the present invention to be incorporated in knee braces which fit human limbs within a wide range of sizes.

These and further objects will be evident from the following disclosure, taken along with the accompanying drawings, which illustrate the preferred embodiment of the joint.

BRIEF DESCRIPTION OF THE DRAWINGS

Further details are explained below with the help of the examples illustrated in the attached drawings in which:

FIG. 1 is a side elevational view of a joint structure according to the present invention for the lateral side member of a brace designed for use on the left knee, showing the joint locked in its fully extended position;

FIG. 2 is a cross-section II—II from FIG. 1;

FIG. 3 is a frontal elevational view showing fragmentary portions of a brace designed for use on the left leg, the brace having a lateral side member according to FIG. 1 and a medial side member;

FIGS. 4 and 5 are side elevational views of the joint structure according to FIG. 1 in each of which the joint elements are moved to a configuration which they may obtain during the flection of a wearer's knee joint; and FIG. 6 is a side elevational view of the joint structure according to FIG. 1 showing the upwardly extending joint element and a fragment of the downwardly extending joint element, a second position of the upwardly extending joint element being superimposed in dashed lines.

Like reference characters indicate corresponding parts throughout the several views of the drawings.

DESCRIPTION OF THE PREFERRED EMBODIMENT

The present joint structure is designed to simulate closely the natural movement of the human knee joint. The articulating surfaces of this joint offer no restraint to its movements. Rather, restraining ligaments are required to restrict the movements of the knee joint to practically one plane while the axis around which motion takes place shifts its position slightly during flection and extension of the joint.

Referring now to the drawings, the present joint structure indicated generally by the reference numeral 10 comprises a pair of pivotally interconnected joint elements 11 and 21. As is shown in FIGS. 2 and 3, the upper end of the joint element 21 is forked, having a generally flat section of a ramp member 23 sandwiched between a pair of furcations 24, 25. The furcations define generally parallel plates which overlap a concave edge surface 29 on the ramp member 23. A head 12 of the joint element 11 is received between the plates for articular motion of the upper joint element 11 relative to the lower joint element 21 within a plane parallel to the planes of these plates. Preferably, the joint element 11, the ramp member 23, and the furcations 24, 25 are formed of stainless steel or the like; and a thin film lubricant is applied to the interfaces between the head and the furcations to reduce friction therebetween.

An elongated slot 15 and apertures 26 formed in the head 12 and in the furcations 24, 25, respectively, are adapted to receive a pivot pin 27 such as a rivet. In the preferred embodiment, the rivet is made of stainless steel; and its shaft measures, by way of example, ¼ inch in outer diameter. The position of the pin 27 is fixed with respect to the furcations 24, 25. As illustrated in the drawings, the pin 27 may be rivetted in place, with the end opposite the head 28 being enlarged to hold the furcations 24, 25 and the joint element 11 in assembled relationship.

The elongated slot is angled rearwardly and downwardly at an angle slightly greater than 90 degrees to the longitudinal axis of the joint element 11. The orientation of the slot with respect to this axis and the radius of curvature of the edge surfaces of its central portion are approximately the same as those of the forward portion 14 of the lower edge surface of the head 12 so that the centerline of the slot is disposed substantially parallel to the forward portion 14 of this edge surface (FIG. 6). Further, the curvature of the forward portion 14 and its angling rearwardly and downwardly simulates the periphery of a short cross-section of the lower surface of the condyle of the human knee joint, the same radius of curvature having been found in numerous X-rays taken in profile of legs belonging to individuals otherwise exhibiting wide variations in size. As a consequence, when the pin 27 moves in the slot 15 from the upper end portion 16 to the lower end portion 17, the length of the joint structure 10 increases by approximately the same amount as does a natural leg.

To reproduce the preferred embodiment of the joint element 11 illustrated in the drawings, one may construct a pattern for it by drawing two parallel lines $\frac{3}{4}$ inch apart, next scribing a first arc having a 2 inch radius about a point located on one of these lines, and then striking a second arc of $1\frac{5}{8}$ inch radius about the same point. The intersection of the line passing through this point and the second arc is the center of the radius of curvature of the outer edge surface of the rearwardly projecting lobe 13 defined by the head 12. This semi-circular outer edge surface forms a continuation of the forward portion 14 of the lower edge surface of the head; the transition between the forward portion 14 and the semi-circular section occurs at the juncture of the first arc and the line which passes through the point which is its center of curvature. Further, the intersection of this line and the second arc is also the center of rotation of the joint elements when the pin 27 abuts the lower end portion 17 of the slot (FIG. 4). The second arc, of $1\frac{5}{8}$ inch radius, is along the centerline of the slot and extends $\frac{3}{8}$ inch from the center of curvature of the lower end portion 17 to the center of curvature of the upper end portion 16. The edge surfaces of the slot 15 itself are located approximately $\frac{1}{8}$ inch on either side of this centerline.

As is illustrated in FIGS. 5 and 6, the radius of curvature and orientation of the concave edge surface 29 with respect to the longitudinal axis of the lower joint element 21 is such that a substantial section of the forward portion 14 of the lower edge surface remains in sliding contact with the concave edge surface 29 as the pin 27 moves along an arc which subtends an angle less than approximately 25 degrees, that is, within the normal angular movement of the knee joint during walking. The highest degree of positive control of the movements of the joint elements is maintained when the wearer flexes his leg through an angle A which is no greater than 14 degrees (FIG. 6). To achieve the requisite high degree of contact between the contiguous edge surfaces of the joints elements 11, 21, the concave edge surface 29 has approximately the same radius of curvature as does the forward portion 14 and the centerline of the slot 15. Thus, the axis around which motion takes place can glide, shifting from the upper to the lower end portion of the slot 15 before the lower edge surface of the upper joint element 11 begins to roll on the concave edge surface 29.

As a consequence, there are present ample frictional forces to prevent the knee from collapsing when a wearer using the brace to support a weakened knee joint inadvertently relaxes his muscles and shifts his weight onto it while standing, especially since the joint movement in such a case is along an arc subtending an angle A less that 14 degrees. Indeed, if a wearer wishes to flex the joint structure 10 in order to walk, he must first lift his upper leg a sufficient distance upwardly but at an angle of flection which is well within the normal range which the average person raises his upper leg when walking. For the wearer of a prosthesis incorporating the joint structure 10, these actions of the joint elements 11, 21 freeing themselves when the upper leg is lifted and then rotating apart automatically and locking in the fully extended position when the wearer sets his heel down means that a normal walking gait can be attained.

In the preferred embodiment illustrated in FIG. 3, joint structures 10, 50, according to the present invention, are incorporated in the lateral and medial side members, respectively, of a knee brace. The centrally disposed regions of the joint structures 10, 50 contiguous the furcations 24, 25; 54, 55, respectively, are approximately mirror images of each other including the positioning of the pins 27 so that their respective heads 28 can be directed away from the knee. Furthermore, like the furcations 24, 25 which are secured to the upper end section 22 of the ramp member 23 by the rivets 32, 33, the furcations 54, 55 are rivetted to the upper end section 52 of the ramp member 53. Beyond these centrally disposed regions, however, the upper joint elements 11, 51, including sections thereof which are attached to the upwardly extending uprights 31, 61, respectively, by the rivets 37, 38, 39, have differing shapes and sizes not only to follow the contour of the human knee joint but also to fit variations between individuals. Similarly, sections of the ramp members 23, 53 distal these centrally disposed regions, including those sections attached by rivets 34, 35, 36 to the downwardly extending uprights 41, 71, respectively, must be properly sized and shaped to meet individual requirements.

The use of connected lateral and medial side members as illustrated in FIG. 3 is preferred in any application in which lateral-medial stability must be maintained, as in a walking cast or in a orthosis used in the rehabilitation of a damaged or diseased knee joint. In such applications, the distal ends of the uprights 31, 61 and 41, 71 are rigidly attached by means of rivets (not shown) to plastic sheet members 65, 66, respectively. Alternately, the distal ends of the uprights may be inserted into pockets formed in the plastic sheet members. The plastic sheet members are preferably composed of a thermoplastic material which may be heated and shaped to conform to the contours of an individual user's limb. The plastic sheet members 66, 65 encircle portions of the thigh and calf, respectively, of a user's leg with each of these members being secured in place by a nonelastic strap 64, 63 having a Velcro fastener incorporated therein. Alternately, the plastic sheet members may be secured to a wearer's limb by means of a tape (not shown) having plaster of Paris embedded in it such as the Hexcelite Orthopaedic Tape to form a cast.

What is claimed is:

1. A joint structure for use in knee braces and the like, comprising:

upper and lower joint elements; the lower joint element having a ramp member and a pair of furcations, both of the furcations overlapping a concave edge surface of the ramp member; the upper joint element having a head which is received between the furcations for articular motion of the upper joint element relative to the lower joint element; the forward portion of the lower edge surface of the head and said concave edge surface having approximately the same radius of curvature;

the upper joint element having an elongated slot formed within said head; the lower joint element having a pin passing through said slot and connecting said joint elements together, the elongated slot having lower and upper end portions adapted to engage said pin and a central portion having curved edge surfaces with approximately said radius of curvature; the central portion being dimensioned to permit said pin to slide between said slot end portions as said joint elements rotate with respect to each other at the same time the forward portion of the lower edge surface of the head engages the concave edge surface of the ramp member, the pin moving within the slot toward the upper end portion thereof as the angle between the longitudinal axes of the joint elements is increased; the joint structure being locked with respect to any further increase in the angle between the longitudinal axes of the upper and lower joint elements when the pin engages the upper end portion;

the head defining a rearwardly projecting lobe, the outer edge surface of the lobe having a substantially smaller radius of curvature than does the concave edge surface of the ramp member; the lower end portion of the slot being arranged on said upper joint element so that when the pin engages, said lower end portion, the pin is positioned at approximately the center of curvature of the outer edge surface of the lobe; the pin being the center of rotation about which the joint elements can rotate as the angle between their longitudinal axes is decreased beyond a limiting angle which is attained when the pin engages the lower end portion of the slot, the limiting angle being substantially less than 180° and being within the range of angles between said longitudinal axes which are traversed as the upper and lower joint elements undergo motions which are encountered when a wearer of the joint structure is using it to approximate a normal walking gait; the upper joint element being rotatable about the pin to decrease the angle between said longitudinal axes even when the lower joint element is stationary once the angle between said longitudinal axes is less than the limiting angle, thereby facilitating a wearer's actions in sitting down;

the forward portion of the lower edge surface being curved downwardly and rearwardly at approximately the same angle to the longitudinal axis of the upper joint element as is the concave edge surface to the longitudinal axis of the lower joint element, so that sliding contact is maintained between substantial sections of the forward portions of the lower edge surface and the concave edge surface when the angle between the longitudinal axes of the joint elements is greater than said limiting angle, thereby preventing an accidental rotation of the joint elements toward each other when the contiguous edge surfaces of the joint elements are not under compression.

2. The joint structure according to claim 1 wherein the length of the joint structure increases continuously as the pin moves in the slot from the upper end portion to the lower end portion but remains approximately constant once the pin engages the lower end portion, thereby imitating the motion of the natural leg throughout flection.

* * * * *